United States Patent
Stutzmann et al.

(10) Patent No.: US 6,380,173 B1
(45) Date of Patent: Apr. 30, 2002

(54) USE OF LOW-MOLECULAR-WEIGHT HEPARINS FOR THE PREVENTION AND TREATMENT OF TRAUMA OF THE CENTRAL NERVOUS SYSTEM

(75) Inventors: Jean-Marie Stutzmann, Villecresnes; André Uzan; Florence Wahl, both of Paris, all of (FR)

(73) Assignee: Aventis Pharma S.A., Cedx (FR)

( * ) Notice: Subject to any disclaimer, the term of this patent is extended or adjusted under 35 U.S.C. 154(b) by 0 days.

(21) Appl. No.: 09/448,244

(22) Filed: Nov. 24, 1999

Related U.S. Application Data

(63) Continuation of application No. PCT/FR98/01034, filed on May 25, 1998.

(30) Foreign Application Priority Data

May 25, 1997 (FR) .............................. 97 06550

(51) Int. Cl.⁷ ........................ A61K 31/715; A01N 43/04
(52) U.S. Cl. ....................................... 514/56
(58) Field of Search ............................. 514/56

(56) References Cited

U.S. PATENT DOCUMENTS 5,605,891 A * 2/1997 Prino et al. .................. 514/56

FOREIGN PATENT DOCUMENTS

| EP | 0 101 141 | 2/1994 |
|---|---|---|
| EP | 0 582 330 | 2/1994 |
| EP | 0 287 477 | 10/1998 |
| WO | WO 92 11294 | 7/1992 |

OTHER PUBLICATIONS

Gorio et al., Glycosaminoglycans in nerve injury: Ii. Effects on transganglionic degeneration and on the expression of neurotrophic factors., J. Neuroscience Research 1996, 46/S, 572–580.

Eckenstein et al., Acidic and basic fibroblast growth factors in the nervous system: Distribution and differential alteration of levels after injury of central versus peripheral nerve, J. Neuroscience. 1991, 11/2, 412–419.

Green et al., Prevention of thromboembolism after spinal cord injury using low molecular weight heparin., Annals of Internal Medicine. 113(8):571–574 (Oct. 15, 1990.

Kay et al., Low molecular weight heparin for the treatment of acute ischemic stroke., New England J. of Med. 1995, 333/8 1588–1593.

* cited by examiner

*Primary Examiner*—Shep K. Rose
*Assistant Examiner*—Donna Jagoe
(74) *Attorney, Agent, or Firm*—Irving Newman

(57) ABSTRACT

Trauma of the central nervous system is prevented and treated by administering an effective amount of a low molecular weight heparin.

12 Claims, No Drawings

USE OF LOW-MOLECULAR-WEIGHT HEPARINS FOR THE PREVENTION AND TREATMENT OF TRAUMA OF THE CENTRAL NERVOUS SYSTEM

This application is a continuation of international application No. PCT/FR98/01034, filed May 25, 1998.

The present invention relates to the use of low-molecular-weight heparins for the prevention and treatment of trauma of the central nervous system and in particular of spinal, cranial or craniospinal trauma.

The invention also relates to the use of low-molecular-weight heparins for the preparation of a medicament for the prevention and treatment of trauma of the central nervous system and in particular of spinal, cranial or craniospinal trauma.

Standard heparin is a sulphated polysaccharide having an average molecular weight of 12,000–15,000 daltons which is isolated from bovine, ovine and porcine intestinal mucous membranes. Heparin is clinically used for the prevention and treatment of thromboembolic disorders but sometimes causes haemorrhages.

Over the past ten years, heparin has been gradually replaced by low-molecular-weight heparins which no longer exhibit or which exhibit to a lesser degree the disadvantage of causing bleeding and which now require only one injection per day instead of 2 to 3 injections per day for standard heparin. These low-molecular-weight heparins are prepared in particular by fractionation, controlled depolymerization of heparin or by chemical synthesis. They have an anti-Xa activity/anti-IIa activity ratio greater than 2.

It has now been found that low-molecular-weight heparins reduce the size of the trauma of the central nervous system and in particular of spinal, cranial or craniospinal trauma.

Traumas of the central nervous system (SNC trauma or neurotrauma) relate to trauma of the brain (cerebral trauma) and traumas of the spinal cord (medullary trauma). They are the consequence of a shock at the level of the central nervous system (car, motorbike, skiing or swimming-pool accident and the like) which is often but not always accompanied by fractures. The consequences of these traumas are neurological disorders such as epilepsy, impairment of consciousness, motor problems, amnesia, aggressiveness and psychoaffective deficiency.

According to the invention, a low-molecular-weight heparin having an average molecular weight of between 1000 and 10,000 daltons, in particular between 1500 and 6000 daltons, and in particular between 4000 and 5000 daltons is preferably used.

They can be prepared by various processes from heparin:

fractionation by means of solvents (FR 2,440,376, U.S. Pat. No. 4,692,435), fractionation on an anionic resin (FR 2,453,875), gel filtration (BARROWCLIFFE, Thromb. Res. 12, 27–36 (1977), affinity chromatography (U.S. Pat. No. 4,401,758), depolymerization controlled by means of a chemical agent: nitrous acid (EP 14184, EP 37319, EP 76279, EP 623629, FR 2,503,714, U.S. Pat. No. 4,804,652; WO 813276), ?-elimination from a heparin ester (EP 40144, U.S. Pat. No. 5,389,618), periodate (EP 287477), sodium borohydride (EP 347588, EP 380943), ascorbic acid (U.S. Pat. No. 4,533,549); hydrogen peroxide (U.S. Pat. No. 4,629,699, U.S. Pat. No. 4,791,195), quaternary ammonium hydroxide from a quaternary ammonium salt of heparin (U.S. Pat. No. 4,981,955), alkali metal hydroxide (EP 380943, EP 347588) or by an enzymatic route (EP 64452, U.S. Pat. No. 4,396,762, EP 244235, EP 244236; U.S. Pat. No. 4,826,827; U.S. Pat. No. 3,766,167); by means of irradiation (EP 269981).

Some can also be prepared by chemical synthesis (U.S. Pat. No. 4,801,583, U.S. Pat. No. 4,818,816, EP 165134, EP 84999, FR 2,535,306).

Among these low-molecular-weight heparins, there may be mentioned more particularly enoxaparin (INN) marketed by RHONE-POULENC RORER, nadroparin (INN) marketed by SANOFI, parnaparin (INN) marketed by OPOCRIN-ALFA, reviparin (INN) marketed by KNOLL, dalteparin (INN) marketed by KABI PHARMACIA, tinzaparin (INN) marketed by NOVO NORDISK, danaparoid (INN) marketed by ORGANON, ardeparin (INN) developed by WYETH AYERST, certoparin (INN) marketed by SANDOZ and products under study such as CY222 from SANOFI-CHOAY (Thromb. Haemostasis, 58 (1), 553 (1987)), SR90107/ORG31540 from SANOFI-ORGANON (Thrombosis and Haemostasis, 74, 1468–1473 (1995)).

Preferably, the low-molecular-weight heparins consist of oligosaccharides having a 2-O-sulpho-4-enopyranosuronic acid at one of their ends.

A particularly advantageous low-molecular-weight heparin is obtained by depolymerization of a heparin ester by means of a base such as sodium hydroxide.

The effect of low-molecular-weight heparins on trauma of the central nervous system is demonstrated in rats on trauma induced according to the following technique: male Sprague-Dawley rats (Charles River France) weighing 280–300 g (13 for the control group and 13 for the treated group) are anaesthetized with halothane (1.5%) in an $N_2O/O_2$ (70/30) mixture and placed in a stereotaxic frame. The epicranium is incised and a hole is made by means of a toothed drill at the level of the right parietal cortex (coordinates: 3.5 mm before, 6 mm above the interaural line). A polyethylene tube with an internal diameter of 3 mm is placed on the dura mater, fixed in the cranial cavity with dental cement and connected to a solenoid valve (Danfoss Evsi 24 V, 15 W). The dura mater is kept intact. The valve is connected to a HPLC pump (Walters 590). The system is filled with sterile water and when the pump has reached a pressure of 3.8 to 4 bar, the fluid impact of moderate severity (1.6–1.8 bar) is induced by a brief opening (20 ms) of the valve. The tube is then withdrawn, the incision sutured and the animals are returned to their cage in a room heated to 26–28?C.

The low-molecular-weight heparins dissolved in a saline solution (0.9% NaCl) are administered in the following manner:

2 hours after the lesion: 0.5 mg/kg/5 ml IV bolus, 2 hours 15 minutes after the lesion: 1 mg/kg/5 ml SC, 6 hours after the lesion: 1 mg/kg/5 ml SC, 24 hours after the lesion: 1 mg/kg/5 ml SC and 30 hours after the lesion: 1 mg/kg/5 ml SC.

5 ml/kg of a saline solution (0.9% NaCl) are administered to the control group under the same conditions.

The animals are sacrificed one week after the trauma and the size of the trauma is evaluated histologically. Coronal sections are stained with a haematoxylin/eosin mixture and the surface areas of the trauma are measured with an image analyser.

In this test, the low-molecular-weight heparins reduce the size of the cerebral trauma by at least 40%.

Enoxaparin (LOVENOX®) reduces the size of the cerebral trauma by 50%.

The medicaments consist of a salt (preferably sodium or calcium) of a low-molecular-weight heparin in the form of a composition in which it is combined with any other pharmaceutically compatible product which may be inert or physiologically active. The medicaments according to the invention may be used by the intravenous, subcutaneous, oral, rectal, topical or pulmonary (inhalation) route.

Sterile compositions for intravenous or subcutaneous administration are generally aqueous solutions.

These compositions may also contain adjuvants, in particular wetting, isotonizing, emulsifying, dispersing and stabilizing agents. The sterilization can be carried out in several ways, for example by aseptisizing filtration, by incorporating sterilizing agents into the composition, by irradiation. They may also be prepared in the form of sterile solid compositions which may be dissolved at the time of use in sterile water or any other injectable sterile medium.

As solid compositions for oral administration, there may be used tablets, pills, powders (gelatine capsules, cachets) or granules. In these compositions, the active ingredient is mixed with one or more inert diluents such as starch, cellulose, sucrose, lactose or silica, under an argon stream. These compositions may also comprise substances other than diluents, for example one or more lubricants such as magnesium stearate or talc, an agent promoting oral absorption, a colorant, a coating (sugar-coated tablets) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavouring or stabilizing products.

The compositions for rectal administration are suppositories or rectal capsules which contain, in addition to the active ingredient, excipients such as cocoa butter, semisynthetic glycerides or polyethylene glycols.

The compositions for topical administration may be, for example, creams, lotions, collyria, collutoria, nasal drops or aerosols.

The doses depend on the desired effect, the duration of treatment and the route of administration used; they are generally between 0.2 mg and 4 mg per kg per day by the subcutaneous route, that is to say 14 to 280 mg per day for an adult.

In general, the doctor will determine the appropriate dosage according to the age, weight and any other factors specific to the subject to be treated.

What is claimed is:

1. A method for the prophylaxis or treatment of craniospinal, spinal or cerebral swelling or trauma of the central nervous system in a mammal in need thereof, this method consisting essentially of administering to said mammal low molecular weight heparin having an average molecular weight of between 1,000 and 10,000 Daltons.

2. The method of claim 1, wherein said trauma of the central nervous system is spinal trauma.

3. The method of claim 1, wherein said trauma of the central nervous system is cranial trauma.

4. The method of claim 1, wherein said trauma of the central nervous system is craniospinal trauma.

5. The method of claim 1, wherein said low-molecular-weight heparin has an average molecular weight of between 1500 and 6000 daltons.

6. The method of claim 5, wherein said low-molecular-weight heparin has an average molecular weight of between 4000 and 5000 daltons.

7. The method of claim 1, wherein said low-molecular-weight heparin comprises oligosaccharides having a 2-O-sulpho-4-enopyranosuronic acid at one of their ends.

8. The method of claim 1, wherein said low-molecular-weight heparin is obtained by depolymerization of a heparin ester by means of a base.

9. The method of claim 1 wherein said trauma of the central nervous system is cerebral trauma.

10. The method of claim 1 wherein said trauma of the central nervous system is medullary trauma.

11. The method of claim 9 wherein said cerebral trauma is reduced by at least 40%.

12. The method of claim 1 wherein said low-molecular-weight heparin is selected from a group consisting of enoxaparin, nadroparin, pamaparin, reviparin, dalteparin, tinzaparin, danaparoid, ardeparin, certoparin, CY222 and SR90107.

* * * * *

UNITED STATES PATENT AND TRADEMARK OFFICE
CERTIFICATE OF CORRECTION

PATENT NO. : 6,380,173 B1
DATED : April 30, 2002
INVENTOR(S) : Stutzmann, Jean-Marie, Uzan, André and Wahl, Florence It is certified that error appears in the above-identified patent and that said Letters Patent is hereby corrected as shown below:

<u>Title page,</u>
Item [30], Foreign Application Priority Data, should read -- May 28, 1997 --.

Signed and Sealed this

Twentieth Day of December, 2005

JON W. DUDAS
*Director of the United States Patent and Trademark Office*